(12) United States Patent
DaSilva et al.

(10) Patent No.: US 6,419,484 B1
(45) Date of Patent: Jul. 16, 2002

(54) OPTICAL COHERENCE TOMOGRAPHY GUIDED DENTAL DRILL

(75) Inventors: Luiz B. DaSilva, Danville; Bill W. Colston, Jr., Livermore; Dale L. James, Tracy, all of CA (US)

(73) Assignee: The Regents of the University of California, Oakland, CA (US)

( * ) Notice: Subject to any disclaimer, the term of this patent is extended or adjusted under 35 U.S.C. 154(b) by 113 days.

(21) Appl. No.: 09/660,036

(22) Filed: Sep. 12, 2000

(51) Int. Cl.$^7$ ................................................ A61C 1/00
(52) U.S. Cl. ...................................................... 433/29
(58) Field of Search ........................... 433/29, 131, 132, 433/125; 356/345

(56) References Cited

U.S. PATENT DOCUMENTS

| | | | | |
|---|---|---|---|---|
| 5,049,070 A | * | 9/1991 | Ademovic | 433/29 |
| 5,178,536 A | * | 1/1993 | Werly et al. | 433/29 |
| 5,290,168 A | * | 3/1994 | Cooper et al. | 433/29 |
| 5,321,501 A | | 6/1994 | Swanson et al. | 356/345 |
| 5,459,570 A | | 10/1995 | Swanson et al. | 356/345 |
| 5,570,182 A | | 10/1996 | Nathel et al. | 356/345 |
| 5,634,790 A | * | 6/1997 | Pathmanabham | 433/29 |
| 5,894,620 A | * | 4/1999 | Polaert et al. | 433/29 |
| 6,179,611 B1 | * | 1/2001 | Evert et al. | 433/29 |

OTHER PUBLICATIONS

B.L. Danielson et al, Guided–Wave Reflectometry with Micrometer Resolution, Applied Optics, vol. 26, No. 14, Jul. 15, 1987.

M.J. Everett et al, Birefringence Characterization of Biological Tissue by Use of Optical Coherence Tomography, Optics Letters, vol. 23, No. 3, Feb. 1, 1988.

R.C. Youngquist et al, Optical Coherence–Domain Reflectometry: A New Optical Evaluation Technique, Optical Letters, vol. 12, No. 3, Mar. 1987.

X. Clivaz et al, High–Resolution Reflectometry in Biological Tissues, Optics Letters, vol. 17, No. 1, Jan. 1, 1992.

M.R. Hee et al, Polarization–Sensitive Low–Coherence Reflectometer for Birefringence Characterization and Ranging, J.Opt.Soc.Am.B.,vol. 9, No. 6, Jun. 1992.

G.J. Tearney et al, Scanning Single–Mode Fiber Optic Catheter–Endoscope for Optical Coherence Tomography, Optics Letters, vol. 21, No. 7, Apr. 1996.

* cited by examiner

Primary Examiner—Todd E. Manahan
(74) Attorney, Agent, or Firm—L. E. Carnahan; Alan H. Thompson

(57) ABSTRACT

A dental drill that has one or multiple single mode fibers that can be used to image in the vicinity of the drill tip. It is valuable to image below the surface being drilled to minimize damage to vital or normal tissue. Identifying the boundary between decayed and normal enamel (or dentine) would reduce the removal of viable tissue, and identifying the nerve before getting too close with the drill could prevent nerve damage. By surrounding a drill with several optical fibers that can be used by an optical coherence domain reflectometry (OCDR) to image several millimeters ahead of the ablation surface will lead to a new and improved dental treatment device.

25 Claims, 3 Drawing Sheets

OPTICAL COHERENCE TOMOGRAPHY GUIDED DENTAL DRILL

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to dental drills, particularly to improved dental drills having vicinity imaging capability and, more particularly, to dental drills provided with optical fibers connected to an optical coherence domain reflectometry (OCDR) to image several millimeters ahead of the ablation surface.

In dentistry, drills are used to remove cavities and to prepare for restoration and implants. In many cases it would be valuable to image below the surface being drilled to minimize damage to vital normal tissue. Identifying the boundary between decayed and normal enamel (or dentine) would reduce the removal of viable tissue; and identifying the nerve before getting too close with the drill could prevent nerve damage. Thus, there is a need for dental treatment imaging, and such has been accomplished by the present invention using (OCDR).

Optical coherence domain reflectometry is a technique developed by Youngquist et al. in 1987 (Youngquist, R. C. et al., "Optical Coherence-Domain Reflectometry: A New Optical Evaluation Technique," 1987, *Optics Letters* 12(3): 158–160). Danielson et al. (Danielson, B. L. et al., "Guided-Wave Reflectometry with Micrometer Resolution," 1987, *Applied Physics* 26(14): 2836–2842) also describe an optical reflectometer which uses a scanning Michelson interferometer in conjunction with a broadband illuminating source and cross-correlation detection. OCDR was first applied to the diagnosis of biological tissue by Clivaz et al. in January 1992 (Clivaz, X. et al., "High-Resolution Reflectometry in Biological Tissues," 1992, *Optics Letters* 17(1): 4–6). A similar technique, optical coherence tomography (OCT) has been developed and used for imaging with catheters by Swanson et al. in 1994 (Swanson, E. A. et al., U.S. Pat. Nos. 5,321,501 and 5,459,570. Tearney et al. (Tearney, G. J. et al., "Scanning Single-Mode Fiber Optic Catheter-Endoscope for Optical Coherence Tomograph," 1996, *Optics Letters* 21(7): 543–545) also describe an OCT system in which a beam is scanned in a circumferential pattern to produce an image of internal organs. U.S. Pat. No. 5,570,182 to Nathel et al. describes method and apparatus for detection of dental caries and periodontal disease using OCT. However, as OCT systems rely on mechanical scanning arms, miniaturizing them enough to operate on a guidewire would be very difficult.

Polarization effects in an OCDR system for birefringence characterization have been described by Hee et al. (Hee, M. R. et al., "Polarization-sensitive low-coherence reflectometer for birefringence characterization and ranging," *J. Opt. Soc. Am. B*, Vol. 9, No. 6, June 1992, 903–908, and in an OCT system by Everett et al. (Everett, M. J. et al., "Birefringence characterization of biological tissue by use of optical coherence tomography," *Optics Letters*, Vol. 23, No. 3, Feb. 1, 1998, 228–230).

In a prior art OCDR scanning system 10, shown in FIG. 1, light from a low coherence source 12 is input into a 2×2 fiber optic coupler 14, where the light is split and directed into sample arm 16 and reference arm 18. An optical fiber 20 is connected to the sample arm 16 and extends into a device 22, which scans an object 24. Reference arm 18 provides a variable optical delay. Light input into reference arm 18 is reflected back by reference mirror 26. A piezoelectric modulator 28 may be included in reference arm 18 with a fixed mirror 26, or modulator 28 may be eliminated by scanning mirror 26 in the Z-direction. The reflected reference beam from reference arm 18 and a reflected sample beam from sample arm 16 pass back through coupler 14 to detector 30 (including processing electronics), which processes the signals by techniques that are well known in the art to produce back-scatter profile (or "image") on display 32.

The present invention utilizes a drill surrounded with several optical fibers used by an OCDR to image several millimeters ahead of the ablation surface. The OCDR system translates this information into a profile image of the tissue optical properties near the ablation surface. This information can be displayed to the user, or analyzed by software to sound an alarm, or stop the drill when a selected boundary or distance to sensitive tissue, nerve, blood vessel, etc., is reached.

SUMMARY OF THE INVENTION

It is an object of the present invention to enable improved dental drilling procedures.

A further object of the invention is to provide imaging of areas slightly ahead of the ablation area of dental drilling.

A further object of the invention is to provide a method for obtaining images of areas ahead of the ablation area.

It is a further object of the invention to utilize OCDR in combination with a dental drill to enable imaging of areas adjacent the drilling operation.

Another object of the invention is to provide a dental drill with optical fibers connected to an OCDR to enable imaging of areas ahead of the drilling or ablation area.

Another object of the invention is to provide an improved dental drilling system, which includes imaging by the user of the area to be drilled, and to provide an alarm or to stop the drill when a selected boundary or distance from the drilling operation is reached.

Other objects and advantages of the present invention will become apparent from the following description and accompanying drawings. Basically, the invention involves an optical coherence tomography (OCT) guided dental drill. The invention is a dental drill that has one or multiple single-mode fibers that can be used to image in the vicinity of the drill tip. Identifying the boundary between decayed and normal enamel (or dentine) reduces the removal of viable tissue, and identifying the nerve before getting too close with the drill prevents nerve damage. The drill is surrounded with 1, 2,4 or more single-mode optical fibers, which independently couple light from a sample arm of an OCDR system to the tissue to be removed. Light from these OCDR fibers exit the tip and are directed into the hard or soft tissue via small diameter optics (such as gradient index lenses and prisms). The light reflected or scattered from the tissue is then collected by the same optical fibers and detected by the OCDR system, which translates this information into a profile image of the tissue optical properties near the ablation surface. This information can be displayed to the user or analyzed by software to sound an alarm or stop the drill when a selected boundary or distance to sensitive tissue is reached. The invention can use single or multiple OCDR systems (one for each imaging fiber), or can be used with a form of multiplexing.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

Figure 1:
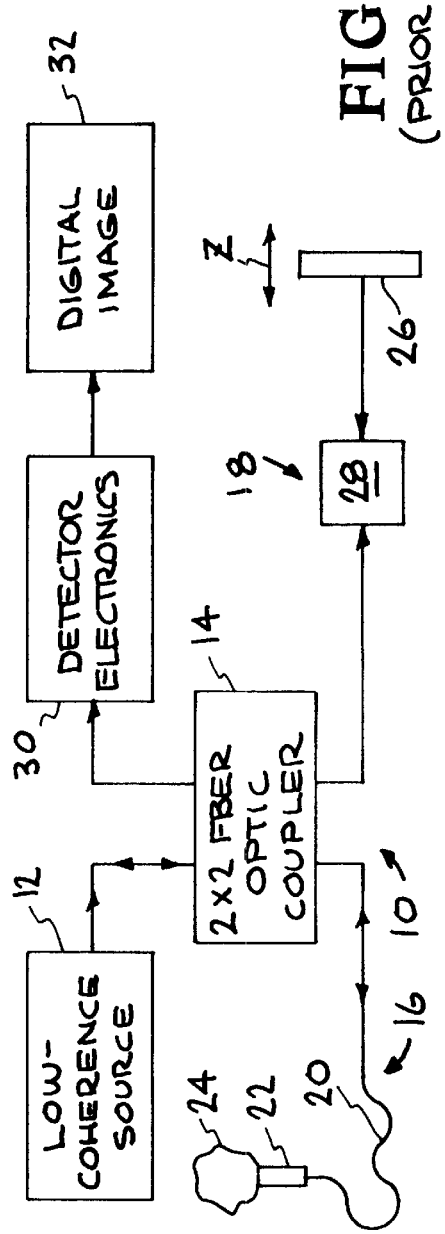
FIG. 1 is a prior art OCDR scanning system.
Figure 2:
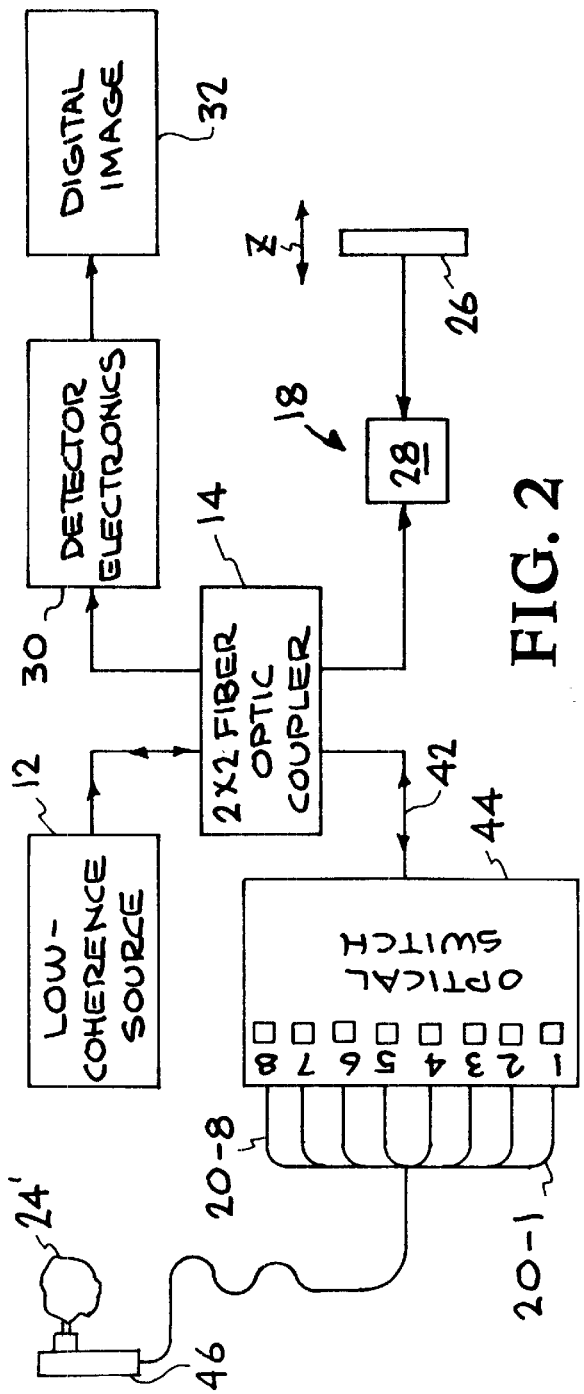
FIG. 2 is a schematic diagram of a dental OCDR optical sensing or guiding system with multiplexed sample arm.

The present invention is an improved dental drilling system which utilizes an optical coherence domain reflectometry (OCDR) system connected via fiber optics to a dental drill which enables imaging of an area in front of the drilling area or ablated surface. This enables the user to identify the boundary between decayed and normal enamel (or dentine) or the boundary adjacent sensitive tissue or the nearness of nerves, etc. Basically, the drill is surrounded with one or more optical fibers connected to an OCDR to image several millimeters ahead of the ablation surface. The 1,2,4 or more single-mode optical fibers that surround the dental drill independently couple light from a sample arm of an OCDR system to the tissue, etc., to be removed. Light from these OCDR fibers exit the drill tip and are directed into the hard or soft tissue via small-diameter optics (such as gradient index lenses and prisms). The light reflected or scattered from the tissue is then collected by the same optical fibers and detected by the OCDR system. The OCDR system translates this information into a profile image of the tissue optical properties near the ablation surface. This information can be displayed to the user or analyzed by software to sound an alarm or stop the ablation of the drill when a selected boundary or distance to sensitive tissue is reached. A single OCDR system consists of a light source split by a beam-splatter or fiber optic coupler into a sample arm and a reference arm. Reflected or back-scattered light from the tissue is collected in the sample arm and detected by heterodyning with light in the reference arm. Only the photons in the sample arm which traveled the same optical path length as the photons in the reference arm (within the coherence length of the source) generate a heterodyne signal. Thus, by varying the path length of the reference beam, and recording the amplitude of the heterodyne signal versus path length, the OCDR system measures the scattering coefficient of the tissue as a function of depth. The present device could use multiple OCDR systems (one for each imaging fiber), or some form of multiplexer. Schematics of a prior art OCDR system and the OCDR guided drill device are shown in FIGS. 1 and 2, with Figures having been described above. The OCDR guided drill device consists of a standard air-driven handpiece, and several single-mode fibers which independently couple light from the sample arm of the OCDE system to the tip of the drill or device. If the device contains more than one OCDR fiber, an optical switch shown in FIG. 2 can be used to switch light between the fibers; or, alternatively, one could have multiple OCDR systems that are controlled and read by a microcontroller or computer. Light emitted from the distal end of each guiding fiber at the tip of the device is directed into the hard or soft tissue via small-diameter optics (such as gradient index lenses or prisms). The small-diameter optics can be adjusted to either probe directly in front of each fiber or, alternatively, to probe at an angle that intercepts the drilling axis at some predetermined distance from the tip. Each fiber would be probing a different region in order to avoid missing important tissue. The information from each fiber probe can then be combined in software to generate an interpolated cross-sectional image of the internal structure of the tissue in the vicinity of the ablation surface.

Referring now to FIGS. 2–5 which illustrate the OCDR guided drill device of the present invention, note that FIG. 2 is generally similar to the prior art OCDR system of FIG. 1, and corresponding components have been given corresponding reference numerals. The OCDR guided drill device of FIG. 2 is generally indicated at 40. The device 40 is based on an OCDR, which has been multiplexed. Except for the multiplexed feature, the system is similar to the prior art system 10 of FIG. 1. Output from a low coherence light source 12 is split at the 2×2 fiber optic coupler 14 and directed through a multiplexed sample arm 42 through optical switch 44 and dental drill 46 toward the sample 24 and through a reference arm 18 to reference mirror 26. Reflections from the mirror 26 and back-scattered light from the sample 24 are recombined at the coupler 14 and propagated to the detector 30 (and light source 12). Constructive interference creates a signal at the detector 30 when the sample and reference reflections have traveled approximately the same optical group delay. The shorter the coherence length of the source, the more closely the sample and reference arm group delays must be matched for constructive interference to occur. By imposing a changing optical delay in the reference arm 18 with a known velocity, either by scanning mirror 26 in the Z-direction or with a piezo-modulator 28 (with fixed mirror 26), the amplitudes and longitudinal positions of reflections from the sample 24 can be measured with high precision. The sample arm 42 contains a multiplexer optical switch 44 for switching between several (e.g., 8) fibers, 20-1 . . . 20-8, allowing sequential spatially distinct regions to be diagnosed consecutively using the same basic OCDR system. One multiplexing technique would be to have the OCDR system scan twice the linear scan range desired (e.g., 10 mm), and then have two probe fibers surround the dental drill that differ in length by 5 mm (see FIG. 6). In this way the first 5 mm of data collected can be assumed to be from the short probe fiber and the second 5 mm of data can be assumed to be from the longer probe fiber. This technique can work because very little or no signal is collected beyond 3–4 mm of tissue, so the data overlap will be negligible. The fibers can be placed anywhere in the dental drill 46. Some fibers can be forward viewing and some can be side viewing, as discussed above.

Figure 3:
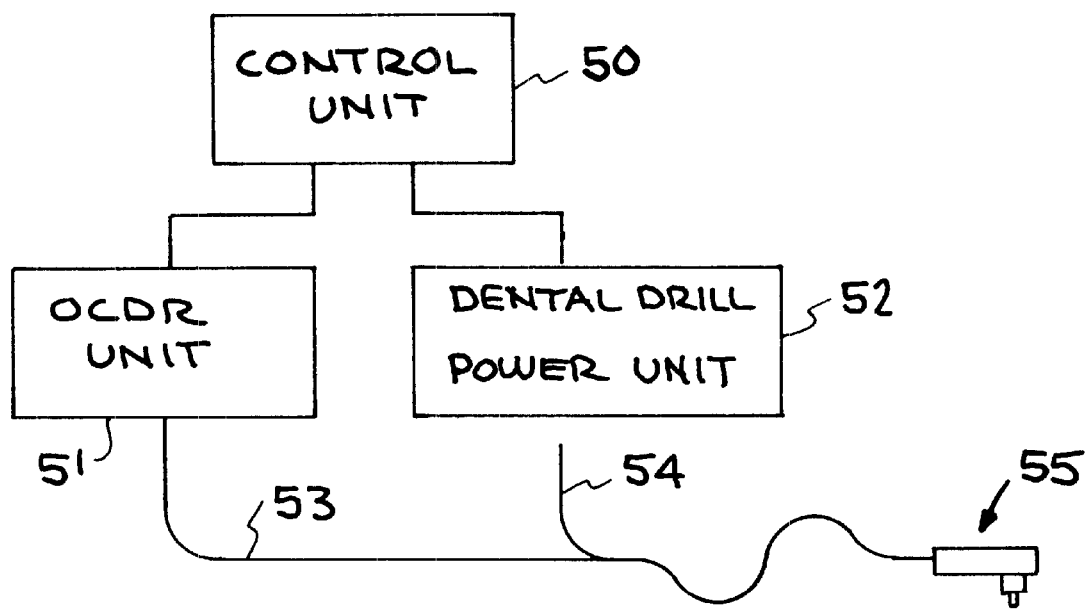
FIG. 3 illustrates the major components of the dental OCDR guiding system made in accordance with the present invention.

FIG. 3 illustrates an overall guided dental drill system which includes a control unit 50 operatively connected to an OCDR unit 51 (such as shown in FIG. 2) and a dental drill power unit 52, with units 51 and 52 connected via appropriate fiber optics, air line, etc., indicated generally at 53 and 54, respectively, to a dental handpiece 55.

Figure 4:
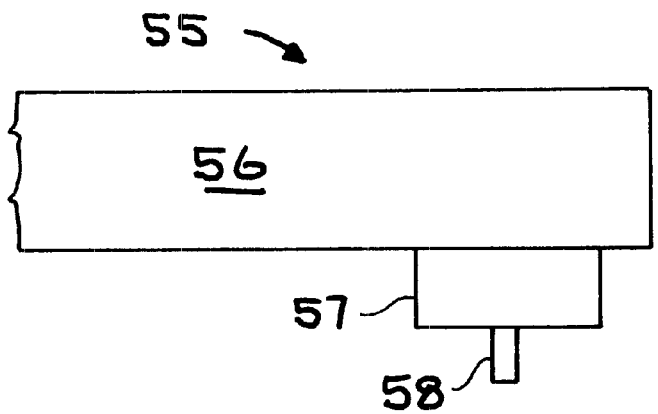
FIG. 4 is an enlarged side view of an embodiment of a dental drill utilized in the invention.
Figure 5:
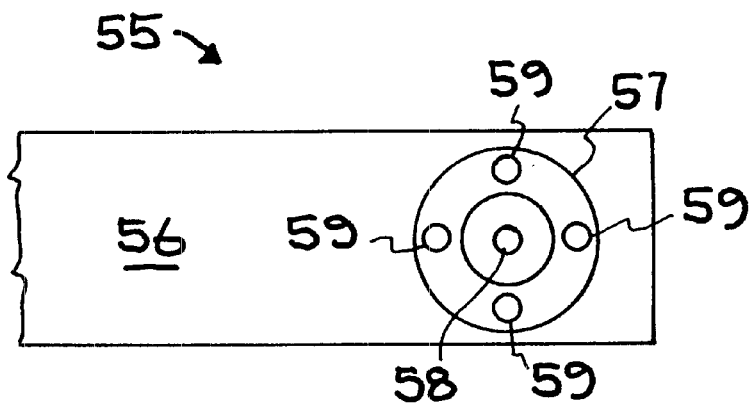
FIG. 5 is a bottom view of the dental drill of FIG. 4 showing the optical fibers mounted about the drill bit.

The dental handpiece 55 of FIG. 3 is shown enlarged in FIGS. 4 and 5 and includes a handle or member 56; an adapter 57; a drill bit 58; and a plurality of fiber optics 59 (4 in this embodiment), the fiber optics 59 being mounted in adapter 57 and extending through handle 56 to the OCDR unit 51, as indicated at 53 in FIG. 3, with the power unit 52 of FIG. 3 providing power to the drill bit 58, as known in the art.

There are a number of possible variants of the OCDR system, most of which have been described in copending U.S. application Ser. No. 09/050,571 (IL-10122) filed Mar. 30, 1998, entitled "Optical Coherence Domain Reflectometry Guidewire," assigned to the same assignee. Also, several alternative embodiments of the OCDR system, including Doppler OCDR, birefringence-sensitive OCDR, and color OCDR, can be used to enhance the contrast of the dental OCDR system of FIGS. 2–5 and obtain other useful clinical information. Doppler OCDR, which provides a measurement of scattered movement as a function of axial position, can be used to quantify blood flow in the gingival tissue and is potentially an indirect method for assessing soft tissue vitality. The birefringence of both hard and soft tissue structures in the oral cavity can be measured using a birefringence-sensitive OCDR system, and is potentially useful for locating decalcified or carious regions in the tooth. A birefringence-sensitive OCT system has been constructed and birefringence of several biological tissues measured. Color OCDR makes use of multiple wavelengths to spectroscopically resolve tissue microstructures based on their wavelength dependent absorption or scattering properties. A dual-wavelength OCDR system has been built and used to measure water concentrations in turbid scattering phantoms.

Figure 6:
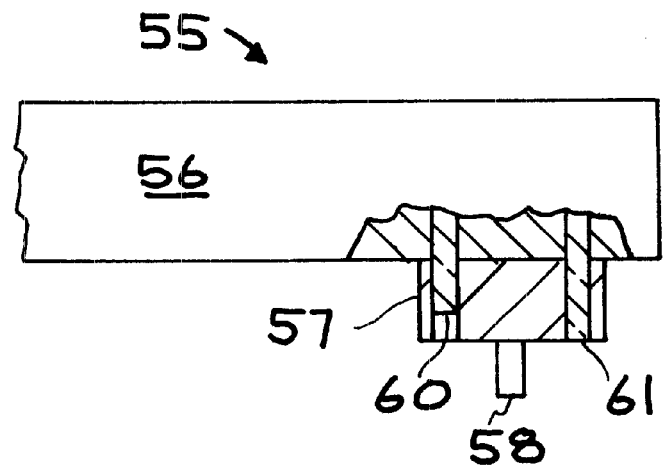
FIG. 6 is an enlarged side view of another embodiment utilizing optical fibers having differing distal end lengths.

FIG. 6 illustrates an embodiment of a drill tip with two optical fibers 60 and 61 positioned such that the distal end of fiber 60 is about 5 mm shorter than the distal end of fiber 61 to produce the multiplexing technique described above.

It has thus been shown that the present invention, which has been developed and experimentally tested, provides a new OCDR device, which is designed to replace the standard dental explorer. The invention provides an OCDR guided dental device for drilling of caries, and can be used to safely guide-drill caries with minimal damage to viable dental tissue. Also, the OCDR guided drill can be used for implant preparation where the implant site is typically prepared by drilling into the bone. During this procedure, it is important to stay at least 1 mm away from the nerve. Having an imaging diagnostic that can image ahead of the drill bit and detect nerve location greatly reduces risk and improves treatment. Since the OCDR guided dental drill of this invention can be used directly by a viewer (the dentist) or incorporated into a system to activate an alarm or shut off the drill, it greatly advances the state of the dental-drilling art.

While specific embodiments have been described and/or illustrated to exemplify and teach the principles of the invention, such are not intended to be limiting. Modifications and changes may become apparent to those skilled in the art, and it is intended that the invention be limited only by the scope of the appended claims.

What is claimed is:

1. A combination of a dental drill and means for imaging the vicinity of the drill tip, said means comprising:
   at least one optical fiber having a distal end and a proximal end,
   said distal end being located adjacent said drill tip,
   an optical coherence domain reflectometry (OCDR) unit,
   said proximal end of said at least one optical fiber being operatively connected to said OCDR unit,
   said at least one optical fiber directing light transmitted therethrough to the vicinity of said drill tip and collecting light reflected back from the vicinity of the drill tip,
   whereby an image in the vicinity of the drill tip is produced.

2. The combination of claim 1, including a plurality of optical fibers having distal ends mounted adjacent said drill tip and proximal ends operatively connected to at least one OCDR unit.

3. The combination of claim 2, wherein said proximal ends are connected to a single OCDR unit via a multiplexer to sequentially switch to each of said optical fibers.

4. The combination of claim 3, wherein said multiplexer comprises an optical switch.

5. The combination of claim 3, whereby light reflected or scattered from tissue located in said vicinity of said drill tip is collected by and transmitted through said plurality of optical fibers and detected by said OCDR unit, whereby this transmitted information is translated by said OCDR unit into a profile image of the tissue optical properties near an ablation surface produced by said drill tip.

6. The combination of claim 5, wherein the profile image can be displayed to a user of the drill tip, or analyzed by computer software to sound an alarm or stop the ablation by the drill tip when a selected boundary or distance to sensitive tissue is reached.

7. The combination of claim 2, wherein said OCDR unit includes a sample arm and a reference arm, said proximal ends of said plurality of optical fibers being operatively connected to said sample arm via a multiplexer, thereby providing said OCDR unit with a multiplexed sample arm.

8. The combination of claim 7, wherein said plurality of optical fibers comprises two fibers having length differences of about 5 mm.

9. The combination of claim 7, wherein said multiplexer comprises an optical switch connected to a proximal end of each of said plurality of optical fibers and constructed to enable switching between said optical fibers allowing sequential spatially distinct regions of the vicinity of said drill tip to be at least imaged by the OCDR.

10. The combination of claim 2, wherein said plurality of optical fibers comprise four optical fibers positioned in an equally spaced arrangement about said drill tip.

11. The combination of claim 2, wherein said plurality of optical fibers are mounted adjacent said drill tip such that a distal end of each optical fiber is directed in a different direction with respect to said drill tip.

12. The combination of claim 1, additionally including a power unit for said dental drill, and a control unit operatively connected to said power unit for said dental drill and operatively connected to said OCDR unit.

13. In a power-driven dental drill system, the improvement comprising a system for imaging an area in front of an ablation surface produced by a drill tip, comprising:
   a plurality of optical fibers having distal ends mounted adjacent said drill tip,
   and an optical coherence domain reflectometer (OCDR) system operatively connected to proximal ends of said plurality of optical fibers.

14. The improvement of claim 13, wherein said proximal ends of said plurality of optical fibers are operatively connected to said OCDR system via a multiplexer.

15. The improvement of claim 13, wherein said distal ends of said plurality of optical fibers are positioned so as to be equally spaced about said drill tip.

16. The improvement of claim 15, wherein said equally spaced distal ends of optical fiber comprises four.

17. The improvement of claim 15, wherein said distal ends of said optical fibers are mounted in different directions with respect to said ablation surface.

18. The improvement of claim 13, wherein said proximal ends of said plurality of optical fiber are operatively connected via an optical switch to a sample arm of said OCDR system.

19. The improvement of claim 13 additionally including a control unit operatively connected to said OCDR system and to said power driven dental drill system.

20. The improvement of claim 13, wherein said OCDR system comprises at least one of a group selected from a single OCDR, a plurality of single OCDR's, a multiplexed OCDR, a Doppler OCDR, a birefringence-sensitive OCDR, a color OCDR and combinations thereof.

21. The improvement of claim 13, wherein said plurality of optical fibers comprises two optical fibers with said distal ends having a length difference of about 5 mm.

22. A method for imaging the vicinity of a dental drill tip, comprising:

providing means for driving the drill tip, providing a plurality of optical fibers having distal ends and proximal ends, positioning the distal ends adjacent the drill tip, providing an optical coherence domain reflectometry (OCDR) unit connecting the proximal ends of the optical fibers to the OCDR unit, and obtaining an image of the vicinity of an ablation area produced by the drill tip.

23. The method of claim 22, wherein obtaining an image is carried out such that an obtained image is of an area in front of an ablation surface produced by the drill tip.

24. The method of claim 22, wherein positioning the distal ends of the optical fibers is carried out by mounting the distal ends in different directions with respect to the ablation area.

25. The method of claim 22, wherein positioning the distal ends of the optical fibers is carried out by mounting the distal ends of two optical fibers so as to have a length difference of about 5 mm, operating the OCDR unit to scan twice a linear scan range of the ablation area, and collecting data from each of the two optical fibers.

* * * * *